(12) United States Patent
Ben-David et al.

(10) Patent No.: US 8,880,192 B2
(45) Date of Patent: Nov. 4, 2014

(54) ELECTRODE CUFFS

(75) Inventors: Tamir Ben-David, Tel Aviv (IL); Noam Gavish, Hod Hasharon (IL); Tsachi Czaczkes, Pardess-Hanna Karkur (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 0 days.

(21) Appl. No.: 13/437,114

(22) Filed: Apr. 2, 2012

(65) Prior Publication Data

US 2013/0261721 A1   Oct. 3, 2013

(51) Int. Cl.
*A61N 1/00*   (2006.01)

(52) U.S. Cl.
USPC ........................................ 607/118

(58) Field of Classification Search
USPC ........................ 607/115–156; 600/373–392
See application file for complete search history.

(56) References Cited

U.S. PATENT DOCUMENTS

| | | |
|---|---|---|
| 3,411,507 A | 11/1968 | Wingrove |
| 3,942,534 A | 3/1976 | Allen |
| 4,010,755 A | 3/1977 | Preston |
| 4,019,518 A | 4/1977 | Maurer et al. |
| 4,026,300 A | 5/1977 | Deluca et al. |
| 4,161,952 A | 7/1979 | Kinney et al. |
| 4,338,945 A | 7/1982 | Kosugi et al. |
| 4,392,496 A | 7/1983 | Stanton |
| 4,465,079 A | 8/1984 | Dickhudt |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. |
| 4,608,985 A | 9/1986 | Chrish et al. |
| 4,628,942 A | 12/1986 | Sweeney et al. |
| 4,632,116 A | 12/1986 | Rosen |
| 4,649,936 A | 3/1987 | Ungar et al. |
| 4,663,102 A | 5/1987 | Brenman et al. |

(Continued)

FOREIGN PATENT DOCUMENTS

| | | |
|---|---|---|
| DE | 198 47 446 | 4/2000 |
| EP | 0 688 577 | 12/1995 |

(Continued)

OTHER PUBLICATIONS

An Office Action dated Jul. 23, 2013, which issued during the prosecution of U.S. Appl. No. 12/947,608.

(Continued)

*Primary Examiner* — Scott Getzow
(74) *Attorney, Agent, or Firm* — Sughrue Mion, PLLC (57) ABSTRACT

An electrode assembly includes electrodes and a cuff, shaped so as to define a tubular housing that defines a longitudinal axis therealong, two edges, and a slit between the two edges. When the housing is closed, respective contact surfaces of the two edges touch each other, and the housing defines an inner surface that faces and surrounds the axis, to which inner surface the electrodes are fixed. The cuff further defines three or more annular insulating elements that extend toward the axis from the inner surface of the housing at respective longitudinal positions along the housing, such that the inner surface of the housing and pairs of the insulating elements define, at respective longitudinal positions along the housing, respective chambers open toward the axis. The housing is shaped such that the contact surfaces of the two edges extend toward the axis and protrude into the chambers.

26 Claims, 4 Drawing Sheets

(56) References Cited

U.S. PATENT DOCUMENTS

| | | |
|---|---|---|
| 4,702,254 A | 10/1987 | Zabara |
| 4,739,764 A | 4/1988 | Lue et al. |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,042,497 A | 8/1991 | Shapland |
| 5,069,680 A | 12/1991 | Grandjean |
| 5,095,905 A | 3/1992 | Klepinski |
| 5,143,067 A | 9/1992 | Rise et al. |
| 5,155,454 A | 10/1992 | Amoroso |
| 5,170,802 A | 12/1992 | Mehra |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker |
| 5,215,086 A | 6/1993 | Terry et al. |
| 5,215,089 A | 6/1993 | Baker, Jr. |
| 5,224,491 A | 7/1993 | Mehra |
| 5,243,980 A | 9/1993 | Mehra |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz |
| 5,334,221 A | 8/1994 | Bardy |
| 5,335,657 A | 8/1994 | Terry et al. |
| 5,344,438 A | 9/1994 | Testerman et al. |
| 5,356,425 A | 10/1994 | Bardy et al. |
| 5,400,784 A | 3/1995 | Durand et al. |
| 5,411,531 A | 5/1995 | Hill et al. |
| 5,423,872 A | 6/1995 | Cigaina |
| 5,437,285 A | 8/1995 | Verrier et al. |
| 5,439,938 A | 8/1995 | Snyder et al. |
| 5,454,840 A | 10/1995 | Krakovsky et al. |
| 5,487,756 A | 1/1996 | Kallesoe et al. |
| 5,505,201 A | 4/1996 | Grill et al. |
| 5,507,784 A | 4/1996 | Hill et al. |
| 5,522,854 A | 6/1996 | Ideker et al. |
| 5,540,730 A | 7/1996 | Terry et al. |
| 5,540,734 A | 7/1996 | Zabara |
| 5,562,717 A | 10/1996 | Tippey et al. |
| 5,562,718 A | 10/1996 | Palermo |
| 5,571,150 A | 11/1996 | Wernicke et al. |
| 5,578,061 A | 11/1996 | Stroetmann et al. |
| 5,597,381 A | 1/1997 | Rizzo, III |
| 5,628,777 A | 5/1997 | Moberg et al. |
| 5,634,462 A | 6/1997 | Tyler et al. |
| 5,645,570 A | 7/1997 | Corbucci |
| 5,658,318 A | 8/1997 | Stroetmann et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry et al. |
| 5,711,316 A | 1/1998 | Elsberry et al. |
| 5,716,385 A | 2/1998 | Mittal et al. |
| 5,755,750 A | 5/1998 | Petruska et al. |
| 5,800,470 A | 9/1998 | Stein et al. |
| 5,824,027 A | 10/1998 | Hoffer et al. |
| 5,832,932 A | 11/1998 | Elsberry et al. |
| 5,833,664 A | 11/1998 | Seare, Jr. |
| 5,833,709 A | 11/1998 | Rise et al. |
| 5,836,994 A | 11/1998 | Bourgeois |
| 5,893,881 A | 4/1999 | Elsberry et al. |
| 5,916,239 A | 6/1999 | Geddes et al. |
| 5,919,220 A | 7/1999 | Stieglitz et al. |
| 5,938,584 A | 8/1999 | Ardito et al. |
| 5,938,596 A | 8/1999 | Woloszko et al. |
| 6,006,134 A | 12/1999 | Hill et al. |
| 6,006,136 A | 12/1999 | Glucksman |
| 6,026,326 A | 2/2000 | Bardy |
| 6,038,477 A | 3/2000 | Kayyali |
| 6,058,331 A | 5/2000 | King et al. |
| 6,066,163 A | 5/2000 | John |
| 6,073,048 A | 6/2000 | Kieval et al. |
| 6,083,249 A | 7/2000 | Familoni |
| 6,086,525 A | 7/2000 | Davey et al. |
| 6,091,977 A | 7/2000 | Tarjan et al. |
| 6,091,992 A | 7/2000 | Bourgeois |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| H1905 H | 10/2000 | Hill |
| 6,134,470 A | 10/2000 | Hartlaub |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,178,349 B1 | 1/2001 | Kieval |
| 6,205,359 B1 | 3/2001 | Boveja |
| 6,230,061 B1 | 5/2001 | Hartung |
| 6,240,314 B1 | 5/2001 | Plicchi et al. |
| 6,266,564 B1 | 7/2001 | Hill et al. |
| 6,272,377 B1 | 8/2001 | Sweeney et al. |
| 6,292,695 B1 | 9/2001 | Webster, Jr. et al. |
| 6,292,703 B1 | 9/2001 | Meier et al. |
| 6,298,268 B1 | 10/2001 | Ben-Haim et al. |
| 6,308,105 B1 | 10/2001 | Duysens et al. |
| 6,317,631 B1 | 11/2001 | Ben-Haim et al. |
| 6,319,241 B1 | 11/2001 | King et al. |
| 6,341,236 B1 | 1/2002 | Osorio et al. |
| 6,356,784 B1 | 3/2002 | Lozano et al. |
| 6,363,279 B1 | 3/2002 | Ben-Haim et al. |
| 6,366,813 B1 | 4/2002 | Dilorenzo |
| 6,381,499 B1 | 4/2002 | Taylor et al. |
| 6,400,982 B2 | 6/2002 | Sweeny et al. |
| 6,405,079 B1 | 6/2002 | Ansarinia |
| 6,434,424 B1 | 8/2002 | Igel et al. |
| 6,445,953 B1 | 9/2002 | Bulkes et al. |
| 6,449,507 B1 | 9/2002 | Hill et al. |
| 6,456,866 B1 | 9/2002 | Tyler et al. |
| 6,463,324 B1 | 10/2002 | Ben-Haim et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,505,082 B1 | 1/2003 | Scheiner et al. |
| 6,511,500 B1 | 1/2003 | Rahme |
| 6,516,227 B1 | 2/2003 | Meadows |
| 6,542,774 B2 | 4/2003 | Hill et al. |
| 6,564,096 B2 | 5/2003 | Mest |
| 6,587,727 B2 | 7/2003 | Osorio et al. |
| 6,600,954 B2 | 7/2003 | Cohen |
| 6,600,956 B2 | 7/2003 | Maschino et al. |
| 6,610,713 B2 | 8/2003 | Tracey |
| 6,622,041 B2 | 9/2003 | Terry, Jr. |
| 6,628,987 B1 | 9/2003 | Hill et al. |
| 6,668,191 B1 | 12/2003 | Boveja |
| 6,671,556 B2 | 12/2003 | Osorio et al. |
| 6,684,105 B2 | 1/2004 | Cohen et al. |
| 6,712,772 B2 | 3/2004 | Cohen et al. |
| RE38,705 E | 2/2005 | Hill et al. |
| 6,850,801 B2 | 2/2005 | Kieval et al. |
| 6,865,416 B2 | 3/2005 | Dev et al. |
| 6,866,657 B2 | 3/2005 | Shchervinsky |
| 6,885,888 B2 | 4/2005 | Rezai |
| 6,895,280 B2 | 5/2005 | Meadows et al. |
| 6,907,293 B2 | 6/2005 | Grill et al. |
| 6,907,295 B2 | 6/2005 | Gross et al. |
| 6,928,320 B2 | 8/2005 | King |
| 6,934,583 B2 | 8/2005 | Weinberg et al. |
| 6,937,897 B2 | 8/2005 | Min et al. |
| 6,985,774 B2 | 1/2006 | Kieval et al. |
| 7,020,530 B1 | 3/2006 | Ideker et al. |
| 7,027,876 B2 | 4/2006 | Casavant et al. |
| 7,050,846 B2 | 5/2006 | Sweeney et al. |
| 7,076,299 B2 | 7/2006 | Thong |
| 7,076,307 B2 | 7/2006 | Boveja et al. |
| 7,087,053 B2 | 8/2006 | Vanney |
| 7,113,816 B2 | 9/2006 | Matsukawa et al. |

(56) References Cited

U.S. PATENT DOCUMENTS

| | | |
|---|---|---|
| 7,123,961 B1 | 10/2006 | Kroll et al. |
| 7,139,607 B1 | 11/2006 | Shelchuk |
| 7,167,748 B2 | 1/2007 | Ben-Haim et al. |
| 7,212,870 B1 | 5/2007 | Helland |
| 7,218,971 B2 | 5/2007 | Heil et al. |
| 7,225,016 B1 | 5/2007 | Koh |
| 7,236,821 B2 | 6/2007 | Cates et al. |
| 7,245,967 B1 | 7/2007 | Shelchuk |
| 7,248,930 B1 | 7/2007 | Woloszko et al. |
| 7,269,457 B2 | 9/2007 | Shafer et al. |
| 7,321,793 B2 | 1/2008 | Ben-Ezra et al. |
| 7,346,398 B2 | 3/2008 | Gross et al. |
| 7,403,819 B1 | 7/2008 | Shelchuk |
| 7,421,297 B2 | 9/2008 | Giftakis |
| 7,460,906 B2 | 12/2008 | Libbus |
| 7,561,922 B2 | 7/2009 | Cohen |
| 7,584,004 B2 | 9/2009 | Caparso et al. |
| 7,627,384 B2 | 12/2009 | Ayal |
| 7,765,000 B2 | 7/2010 | Zhang |
| 7,778,703 B2 | 8/2010 | Gross et al. |
| 7,778,711 B2 | 8/2010 | Ben-David |
| 7,805,203 B2 | 9/2010 | Ben-David |
| 7,809,442 B2 | 10/2010 | Bolea et al. |
| 7,840,266 B2 | 11/2010 | Libbus et al. |
| 7,844,346 B2 | 11/2010 | Cohen |
| 7,885,709 B2 | 2/2011 | Ben-David |
| 7,996,092 B2 | 8/2011 | Mrva et al. |
| 8,116,881 B2 * | 2/2012 | Cohen et al. .............. 607/118 |
| 8,155,757 B1 * | 4/2012 | Neisz et al. .............. 607/118 |
| 8,214,056 B2 | 7/2012 | Hoffer et al. |
| 8,326,438 B2 | 12/2012 | Ayal |
| 2002/0035335 A1 | 3/2002 | Schauerte |
| 2002/0099419 A1 | 7/2002 | Cohen et al. |
| 2002/0107553 A1 | 8/2002 | Hill et al. |
| 2002/0120304 A1 | 8/2002 | Mest |
| 2002/0161415 A1 | 10/2002 | Cohen et al. |
| 2003/0018367 A1 | 1/2003 | DiLorenzo |
| 2003/0040774 A1 | 2/2003 | Terry et al. |
| 2003/0040785 A1 | 2/2003 | Maschino |
| 2003/0045909 A1 | 3/2003 | Gross et al. |
| 2003/0045914 A1 | 3/2003 | Cohen et al. |
| 2003/0050677 A1 | 3/2003 | Gross et al. |
| 2003/0078623 A1 | 4/2003 | Weinberg et al. |
| 2003/0078643 A1 | 4/2003 | Schulman |
| 2003/0097221 A1 | 5/2003 | Chun et al. |
| 2003/0100924 A1 | 5/2003 | Foreman et al. |
| 2003/0100933 A1 | 5/2003 | Ayal et al. |
| 2003/0195574 A1 | 10/2003 | Osorio et al. |
| 2003/0216775 A1 | 11/2003 | Hill et al. |
| 2003/0229380 A1 | 12/2003 | Adams et al. |
| 2003/0233129 A1 | 12/2003 | Matos |
| 2003/0236557 A1 | 12/2003 | Whitehurst et al. |
| 2003/0236558 A1 | 12/2003 | Whitehurst et al. |
| 2004/0006311 A1 | 1/2004 | Shchervinsky |
| 2004/0006331 A1 | 1/2004 | Shchervinsky |
| 2004/0024439 A1 | 2/2004 | Riso |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0172094 A1 | 9/2004 | Cohen et al. |
| 2004/0193231 A1 | 9/2004 | Ben-David et al. |
| 2004/0199210 A1 | 10/2004 | Shelchuk |
| 2004/0215289 A1 | 10/2004 | Fukui |
| 2004/0243182 A1 | 12/2004 | Cohen et al. |
| 2004/0249416 A1 | 12/2004 | Yun et al. |
| 2004/0254612 A1 | 12/2004 | Ben Ezra et al. |
| 2005/0010265 A1 | 1/2005 | Baru et al. |
| 2005/0038490 A1 | 2/2005 | Gross et al. |
| 2005/0065553 A1 | 3/2005 | Ben Ezra et al. |
| 2005/0102007 A1 | 5/2005 | Ayal et al. |
| 2005/0131467 A1 | 6/2005 | Boveja |
| 2005/0149154 A1 | 7/2005 | Cohen et al. |
| 2005/0171577 A1 | 8/2005 | Cohen et al. |
| 2005/0187584 A1 | 8/2005 | Denker et al. |
| 2005/0187586 A1 | 8/2005 | Ben-David et al. |
| 2005/0197675 A1 | 9/2005 | Ben-David et al. |
| 2005/0222644 A1 | 10/2005 | Killian et al. |
| 2005/0261672 A1 | 11/2005 | Deem et al. |
| 2005/0267542 A1 | 12/2005 | Ben-David et al. |
| 2005/0273138 A1 | 12/2005 | To et al. |
| 2006/0015153 A1 | 1/2006 | Gliner et al. |
| 2006/0030919 A1 | 2/2006 | Mrva et al. |
| 2006/0052831 A1 | 3/2006 | Fukui |
| 2006/0074449 A1 | 4/2006 | Denker et al. |
| 2006/0074450 A1 | 4/2006 | Boveja et al. |
| 2006/0100668 A1 | 5/2006 | Ben-David et al. |
| 2006/0106441 A1 | 5/2006 | Ayal et al. |
| 2006/0116739 A1 | 6/2006 | Betser et al. |
| 2006/0129205 A1 | 6/2006 | Boveja et al. |
| 2006/0136024 A1 | 6/2006 | Cohen et al. |
| 2006/0167501 A1 | 7/2006 | Ben-David et al. |
| 2006/0195170 A1 | 8/2006 | Cohen et al. |
| 2006/0206154 A1 | 9/2006 | Moffitt et al. |
| 2006/0206155 A1 | 9/2006 | Ben-David et al. |
| 2006/0206159 A1 | 9/2006 | Moffitt et al. |
| 2006/0217772 A1 | 9/2006 | Libbus et al. |
| 2006/0241697 A1 | 10/2006 | Libbus et al. |
| 2006/0241725 A1 | 10/2006 | Libbus et al. |
| 2006/0241733 A1 | 10/2006 | Zhang et al. |
| 2006/0265027 A1 | 11/2006 | Vaingast et al. |
| 2006/0271108 A1 | 11/2006 | Libbus et al. |
| 2006/0271115 A1 | 11/2006 | Ben Ezra et al. |
| 2006/0271137 A1 | 11/2006 | Stanton-Hicks |
| 2006/0282145 A1 | 12/2006 | Caparso et al. |
| 2007/0027487 A1 | 2/2007 | Mika |
| 2007/0150034 A1 | 6/2007 | Rooney et al. |
| 2007/0162079 A1 | 7/2007 | Shemer et al. |
| 2007/0179543 A1 | 8/2007 | Ben-David et al. |
| 2007/0179558 A1 | 8/2007 | Gliner et al. |
| 2007/0203527 A1 | 8/2007 | Ben-David et al. |
| 2007/0239243 A1 | 10/2007 | Moffitt et al. |
| 2007/0255320 A1 | 11/2007 | Inman et al. |
| 2008/0004673 A1 | 1/2008 | Rossing et al. |
| 2008/0021504 A1 | 1/2008 | McCabe et al. |
| 2008/0065158 A1 | 3/2008 | Ben Ezra et al. |
| 2008/0065184 A1 | 3/2008 | Hoffer et al. |
| 2008/0086180 A1 | 4/2008 | Ben Ezra et al. |
| 2008/0086182 A1 | 4/2008 | Ben-David et al. |
| 2008/0086185 A1 | 4/2008 | Amurthur et al. |
| 2008/0109045 A1 | 5/2008 | Gross et al. |
| 2008/0132983 A1 | 6/2008 | Cohen et al. |
| 2008/0147137 A1 | 6/2008 | Cohen et al. |
| 2008/0161894 A1 | 7/2008 | Ben-David |
| 2008/0161895 A1 | 7/2008 | Gross et al. |
| 2008/0172116 A1 | 7/2008 | Mrva et al. |
| 2008/0234780 A1 | 9/2008 | Smith et al. |
| 2009/0005845 A1 | 1/2009 | David et al. |
| 2009/0259315 A1 | 10/2009 | Banik |
| 2009/0275996 A1 | 11/2009 | Burnes et al. |
| 2010/0010603 A1 | 1/2010 | Ben-David et al. |
| 2010/0042186 A1 | 2/2010 | Ben-David et al. |
| 2010/0042194 A1 | 2/2010 | Ayal et al. |
| 2010/0047376 A1 | 2/2010 | Imbeau et al. |
| 2010/0241195 A1 | 9/2010 | Meadows et al. |
| 2010/0241207 A1 | 9/2010 | Bluger |
| 2010/0312320 A1 | 12/2010 | Faltys et al. |
| 2011/0098796 A1 | 4/2011 | Ben-David et al. |
| 2011/0160827 A1 | 6/2011 | Bonde et al. |
| 2011/0196445 A1 | 8/2011 | Bolea et al. |
| 2011/0202106 A1 | 8/2011 | Bolea et al. |
| 2012/0095540 A1 | 4/2012 | Wahlstrand et al. |
| 2012/0130463 A1 | 5/2012 | Ben-David |
| 2012/0197371 A1 | 8/2012 | Neisz et al. |

FOREIGN PATENT DOCUMENTS

| | | |
|---|---|---|
| EP | 0831954 | 4/1998 |
| EP | 0 865 800 | 9/1998 |
| EP | 1785160 | 5/2007 |
| WO | 96/41655 | 12/1966 |

(56) References Cited

FOREIGN PATENT DOCUMENTS

| WO | 01/10357 | 2/2001 |
|---|---|---|
| WO | 01/10375 | 2/2001 |
| WO | 01/10432 | 2/2001 |
| WO | 01/26729 | 4/2001 |
| WO | 02/22206 | 3/2002 |
| WO | 02/085448 | 10/2002 |
| WO | 02/087683 | 11/2002 |
| WO | 03/018113 | 3/2003 |
| WO | 03/094693 | 11/2003 |
| WO | 03/099373 | 12/2003 |
| WO | 03/099377 | 12/2003 |
| WO | 2004/028624 | 4/2004 |
| WO | 2004/047914 | 6/2004 |
| WO | 2004/052444 | 6/2004 |
| WO | 2004/103455 | 12/2004 |
| WO | 2004/110549 | 12/2004 |
| WO | 2004/110550 | 12/2004 |
| WO | 2006/126201 | 11/2006 |
| WO | 2007/053065 | 5/2007 |
| WO | 2008/007360 | 1/2008 |
| WO | 2008/041233 | 10/2008 |

OTHER PUBLICATIONS

An Office Action dated Jan. 3, 2011 which issued during the prosecution of U.S. Appl. No. 11/978,776.
An Office Action dated May 26, 2011 which issued during the prosecution of U.S. Appl. No. 12/012,366.
An Extended European Search Report dated Jun. 6, 2011 during the prosecution of European Patent Application No. 11002403.1.
Office Action dated May 25, 2009, which issued during the prosecution of Applicant's European Patent Application No. 06255816.8.
Zi-Ping Fang, et al., "Selective Activation of Small Motor Axons by Quasitrapezodial Current Pulses", IEEE Transactions on Biomedical Engineering, vol. 38, No. 2 Feb. 1991.
An Office Action dated Jun. 27, 2008, which issued during the prosecution of Applicant's U.S. Appl. No. 10/205,475.
Baratta R et al., "Orderly stimulation of skeletal muscle motor units with tripolar nerve cuff electrode," IEEE Transactions on Biomedical Engineering, 36(8):836-43 (1989).
Deurloo KE et al., "Transverse tripolar stimulation of peripheral nerve: a modelling study of spatial selectivity," Med Biol Eng Comput, 36(1):66-74 (1998).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Goodall EV et al., "Position-selective activation of peripheral nerve fibers with a cuff electrode," IEEE Trans Biomed Eng, 43(8):851-6 (1996).
An Office Action dated Dec. 2, 2011 which issued during the prosecution of U.S. Appl. No. 12/012,366.
Grill WM et al., "Inversion of the current-distance relationship by transient depolarization," IEEE Trans Biomed Eng, 44(1):1-9 (1997).
Jones, JFX et al., "Heart rate responses to selective stimulation of cardiac vagal C fibres in anaesthetized cats, rats and rabbits," J Physiol 489 (Pt 1):203-14 (1995).
Naples GG et al., "A spiral nerve cuff electrode for peripheral nerve stimulation," by IEEE Transactions on Biomedical Engineering, 35(11) (1988).
Rijkhoff NJ et al., "Orderly recruitment of motoneurons in an acute rabbit model," Ann. Conf. of the IEEE Eng., Medicine and Biology Soc., 20(5):2564 (1998).
Sweeney JD et al., "A nerve cuff technique for selective excitation of peripheral nerve trunk regions," IEEE Transactions on Biomedical Engineering, 37(7) (1990).
Sweeney JD et al., "An asymmetric two electrode cuff for generation of unidirectionally propagated action potentials," IEEE Transactions on Biomedical Engineering, vol. BME-33(6) (1986).
Tarver WB et al., "Clinical experience with a helical bipolar stimulating lead," Pace, vol. 15, October, Part II (1992).
Ungar IJ et al., "Generation of unidirectionally propagating action potentials using a monopolar electrode cuff," Annals of Biomedical Engineering, 14:437-450 (1986).
van den Honert C et al., "A technique for collision block of peripheral nerve: Frequency dependence," MP-12, IEEE Trans. Biomed. Eng. 28:379-382 (1981).
van den Honert C et al., "Generation of unidirectionally propagated action potentials in a peripheral nerve by brief stimuli," Science, 206:1311-1312 (1979).
Veraart C et al., "Selective control of muscle activation with a multipolar nerve cuff electrode," IEEE Trans Biomed Eng, 40(7):640-53 (1993).
Mushahwar VK et al., "Muscle recruitment through electrical stimulation of the lumbo-sacral spinal cord," IEEE Trans Rehabil Eng, 8(1):22-9 (2000).
Rattay, in the article, "Analysis of models for extracellular fiber stimulation," IEEE Transactions on Biomedical Engineering, vol. 36, No. 2, p. 676, 1989.
Rijkhoff NJ et al., "Acute animal studies on the use of anodal block to reduce urethral resistance in sacral root stimulation," IEEE Transactions on Rehabilitation Engineering, 2(2):92 (1994).
Evans M S et al., "Intraoperative human vagus nerve compound action potentials," Acta Neurol Scand 110:232-238 (2004).
Lertmanorat Z et al., "A novel electrode array for diameter-dependent control of axonal excitability: a simulation study," IEEE Transactions on Biomedical Engineering 51(7):1242-1250 (2004).
An Office Action dated Apr. 5, 2007, which issued during the prosecution of Applicant's U.S. Appl. No. 10/488,334.
An Office Action dated Apr. 25, 2008, which issued during the prosecution of Applicant's U.S. Appl. No. 10/488,334.
Jones, et al., "Activity of C fibre cardiac vagal efferents in anaesthetized cats and rats", Journal of Physiology (1998), 507.3, pp. 869-880.
M. Manfredi, "Differential Block of conduction of larger fibers in peripheral nerve by direct current", Arch. Ital. Biol. 108:52-71, 1970.
Fuster and Ryden, et al, "ACC/AHA/ESC Practice Guidlelines", JACC vol. 38, No. 4, 2001.
Bilgutay, et al, "Vagal tuning a new concept in the treatment of supraventricular arrhythmias, angina pectoris, and heart failure", J. Thoracic Cardiovasc. Surg. 56(1): 71-82, Jul. 1968.
Gregory S. Friedrichs, "Experimental models of atrial fibrillation/flutter", Journal of Pharmacological and Toxiligical Methods 43 (2000), 117-123.
Ake Hjalmarson, "Prevention of sudden cardiac death with beta blockers", Clin. Cardiol. 22, (Suppl. V), V-11-V-15, 1999.
Danshi Li, et al, "Promotion of atrial fibrillation by heart failure in dogs", Circulation, Jul. 6, 1999, pp. 87-95.
Herman Kwan, et al, "Cardiovascular adverse drug reactions during initiation of antiarrhythmic therapy for atrial fibrillation", Can J Hosp Pharm 2001:54:10-14.
Lena Jideus, "Atrial fibrillation after coronary artery bypass surgery", Acta Universitatis Upsaliensis, Uppsala 2001.
Cummings JE et al., "Preservation of the anterior fat pad paradoxically decreases the incidence of postoperative atrial fibrillation in humans," J Am Coll Cardiol 43(6):994-1000 (2004).
Carlson MD et al., "Selective stimulation of parasympathetic nerve fibers to the human sinoatrial node," Circulation 85:1311-1317 (1992).
Y. Mang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
Furukawa Y et al., "Differential blocking effects of atropine and gallamine on negative chronotropic and dromotropic responses to vagus stimulation in anesthetized dogs," J Pharmacol Exp Ther. 251(3):797-802 (1989).
Bluemel KM, "Parasympathetic postganglionic pathways to the sinoatrial node," J Physiol. 259(5 Pt 2):H1504-10 (1990).
Bibevski S et al., "Ganglionic Mechanisms Contribute to Diminished Vagal Control in Heart Failure," Circulation 99:2958-2963 (1999).

(56) References Cited

OTHER PUBLICATIONS

Garrigue S et al., "Post-ganglionic vagal stimulation of the atrioventricular node reduces ventricular rate during atrial fibrillation," Pace 21(4), Part II, 878 (1998).
Chen SA et al., "Intracardiac stimulation of human parasympathetic nerve fibers induces negative dromotropic effects: implication with the lesions of radiofrequency catheter ablation," J Cardiovasc Electrophysiol. 9(3):245-52.
Goldberger JJ et al., "New technique for vagal nerve stimulation," J Neurosci Methods. 91(1-2):109-14 (1999).
PagéPL et al., "Regional distribution of atrial electrical changes induced by stimulation of extracardiac and intracardiac neural elements," J Thorac Cardiovasc Surg. 109(2):377-88 (1995).
Mazgalev TN, "AV Nodal Physiology," Heart Rhythm Society (www.hrsonline.org), no date.
Cooper TB et al., "Neural effects on sinus rate and atrial ventricular conduction produced by electrical stimulation from a transvenous electrode catheter in the canine right pulmonary artery" Circ Res vol. 46(1):48-57 (1980).
Waninger MS et al., "Electrophysiological control of ventricular rate during atrial fibrillation," PACE 23:1239-1244 (2000).
An Office Action dated May 18, 2007, which issued during the prosecution of Applicant's U.S. Appl. No. 10/529,149.
Supplementary European Search Report dated Nov. 4, 2009, which issued during the prosecution of Applicant's European App No. 03723040.
An International Search Report and a Written Opinion both dated Nov. 13, 2003 which issued during the prosecution of Applicant's PCT/IL03/00430.
U.S. Appl. No. 60/263,834, filed Jan. 25, 2001.
Stampfli, Robert, "Saltatory conduction in nerve," Physiol Rev 34 (1954), pp. 101-112.
An International Search Report and a Written Opinion both dated Dec. 23, 2002, which issued during the prosecution of Applicant's PCT/IL02/00068.
An Office Action dated Sep. 28, 2011 which issued during the prosecution of U.S. Appl. No. 12/228,630.
Communication in EP 03723040 dated Aug. 13, 2010.
An Office Action dated Jan. 21, 2011, which issued during the prosecution of U.S. Appl. No. 12/589,132.
An Office Action dated Jun. 7, 2011, which issued during the prosecution of U.S. Appl. No. 12/589,132.
An Office Action dated Apr. 25, 2008, which issued during the prosecution of U.S. Appl. No. 10/488,334.
An Office Action dated Apr. 5, 2007, which issued during the prosecution of U.S. Appl. No. 10/488,334.
An Office Action dated May 18, 2007, which issued during the prosecution of U.S. Appl. No. 10/529,149.
An Office Action dated May 23, 2011, which issued during the prosecution of U.S. Appl. No. 11/978,776.
An Office Action dated May 26, 2011, which issued during the prosecution of U.S. Appl. No. 12/012,366.
An Office Action dated Jun. 17, 2004, which issued during the prosecution of U.S. Appl. No. 10/205,474.
An Office Action dated Oct. 17, 2007, which issued during the prosecution of U.S. Appl. No. 10/948,516.
An Office Action dated Mar. 20, 2009, which issued during the prosecution of U.S. Appl. No. 11/022,011.
An Office Action dated Aug. 31, 2009, which issued during the prosecution of U.S. Appl. No. 11/280,884.
An Office Action dated Jan. 15, 2004, which issued during the prosecution of U.S. Appl. No. 10/205,474.
An Office Action dated Mar. 7, 2007, which issued during the prosecution of U.S. Appl. No. 10/948,516.
An Office Action dated Aug. 6, 2007, which issued during the prosecution of U.S. Appl. No. 11/022,011.
An Office Action dated Oct. 24, 2008, which issued during the prosecution of U.S. Appl. No. 11/022,011.
An Office Action dated Feb. 18, 2009, which issued during the prosecution of U.S. Appl. No. 11/280,884.
An Office Action dated Apr. 28, 2010, which issued during the prosecution of U.S. Appl. No. 11/981,301.
An Office Action dated Jul. 12, 2011, which issued during the prosecution of U.S. Appl. No. 11/981,301.
A Notice of Allowance dated Jul. 31, 2012, which issued during the prosecution of U.S. Appl. No. 12/589,132.
An Office Action dated Nov. 1, 2007, which issued during the prosecution of U.S. Appl. No. 10/205,475.
An International Preliminary Report on Patentability dated Feb. 17, 2005, which issued during the prosecution of Applicant's PCT/IL03/00431.
An International Preliminary Report dated Feb. 23, 2004 which issued during the prosecution of Applicant's PCT/IL03/00430.
An Examination Report dated Oct. 19, 2007, which issued during the prosecution of European Patent Application No. 06255816.
An International Preliminary Report on Patentability dated Nov. 4, 2009, which issued during the prosecution of Applicant's PCT/IL02/00068.
A European Search Report dated Aug. 27, 2009, which issued during the prosecution of Applicant's European Patent Application No. 09 25 1749.
An Office Action dated Dec. 8, 2009, which issued during the prosecution of Applicant's U.S. Appl. No. 11/347,120.
An Office Action dated Aug. 21, 2012, which issued during the prosecution of U.S. Appl. No. 13/271,720.
An Office Action dated Jun. 8, 2012, which issued during the prosecution of U.S. Appl. No. 12/228,630.
An Office Action dated Jul. 30, 2012, which issued during the prosecution of U.S. Appl. No. 11/978,440.
An Office Action dated Nov. 21, 2012, which issued during the prosecution of U.S. Appl. No. 12/952,058.
An Office Action dated May 6 2013, which issued during the prosecution of U.S. Appl. No. 12/947,608.
An Office Action dated Jun. 13, 2013, which issued during the prosecution of U.S. Appl. No. 12/952,058.
Quan KJ, et al., "Endocardial stimulation of efferent parasympathetic nerves to the atrioventricular node in humans: optimal stimulation sites and the effects of digoxin", Journal of Interventional Cardiac Ekectrophysiology 5:145-152, 2001.
Lemery R et al., "Feasibility study of endocardial mapping of ganglionated plexuses during catheter ablation of atrial fibrillation", Heart Rhythm 3:387-396, 2006.
Vincenzi, et al., "Release of autonomic mediators in cardiac tissue by direct subthreshold electrical stimulation", J Pharmacol Exp Ther. Aug. 1963; 141:185-94.
Wallick DW et al., "Selective AV nodal vagal stimulation improves hemodynamics during acute atrial fibrillation in dogs", AM J Physiol Heart Circ Physiol 281:H1490-H1497, 2001.
Zhang Y et al., "Chronic atrioventricular nodal vagal stimulation: first evidence for long-term ventricular rate control in canine atrial fibrillation model", Circulation 112:2904-2911, 2005.
Schaurete P et al., "Ventricular rate control during atrial fibrillation by cardiac parasympathetic nerve stimulation: A transvenous approach", Journal of the American College of Cardiology 34(7): 2043-2050, 1999.
Schaurete P et al., "Catheter stimulation of cardiac parasympathetic nerves in humans: A novel approach to the cardiac autonomic nervous system", Circulation 104: 2430-2435, 2001.
Schaurete P. et al., "Transvenous parasympathetic cardiac nerve stimulation for treatment of tachycardiac atrial fibrillation", Tachycarde Rhythmusstorungen 89:766-773, 2000.
Lazzara R et al., "Selective in situ parasympathetic control of the canine sinuatrial and atrioventricular node", Circulation Research 32:393-401, 1973.
Takei M et al., "Vagal stimulation prior to atrial rapid pacing protects the atrium from electrical remodeling in anesthetized dogs," Jpn Circ J 65(12):1077-81 (2001).
Hayashi H et al., "Different effects of class Ic and III antiarrhythmic drugs on vagotonic atrial fibrillation in the canine heart," Journal of Cardiovascular Pharmacology 31:101-107 (1998).
Masato Tsuboi et al., "Inotropic, chronotropic, and dromotropic effects mediated via parasympathetic ganglia in the dog heart," Am J Physiol Heart Circ Physiol 279: H1201-H1207 (2000).

(56) References Cited

OTHER PUBLICATIONS

Wijffels MC et al., "Atrial fibrillation begets atrial fibrillation," Circulation 92:1954-1968 (1995). Abstract.
Akselrod S et al., "Power spectrum analysis of heart rate fluctuation: a quantitative probe of beat-to-beat cardiovascular control," Science 213: 220-222 (1981).
Billette J et al., "Roles of the AV junction in determining the ventricular response to atrial fibrillation," Can J Physiol Pharamacol 53(4)575-85 (1975).
Higgins CB, "Parasympathetic control of the heart," Pharmacol. Rev. 25:120-155 (1973).
Kamath et al., in "Effect of vagal nerve electrostimulation on the power spectrum of heart rate variability in man," Pacing Clin Electrophysiol 15:235-43 (1992).
Wang H et al., "Nicotinic acetylcholine receptor alpha-7 subunit is an essential regulator of inflammation," Nature 421:384-388 (2003).
Vanoli E et al., "Vagal stimulation and prevention of sudden death in conscious dogs with a healed myocardial infarction," Circ Res 68(5):1471-81 (1991).
Randall WC ed., Neural Regulation of the Heart, Oxford University Press (1977), particularly pp. 100-106.
Martin PJ et al., "Phasic effects of repetitive vagal stimulation on atrial contraction," Circ. Res. 52(6):657-63 (1983).
Morady F et al., "Effects of resting vagal tone on accessory atrioventricular connections," Circulation 81(1):86-90 (1990).
Stramba-Badiale M et al., "Sympathetic-Parasympathetic Interaction and Accentuated Antagonism in Conscious Dogs," American Journal of Physiology 260 (2Pt 2):H335-340 (1991).
An Examination Report dated Feb. 7, 2011, which issued during the prosecution of Applicant's European Patent Application No. 03725560.
A Supplementary European Search Report dated Aug. 16, 2010, which issued during the prosecution of Applicant's European Application No. 03725560.
Hoffer Ja et al., "How to use nerve cuffs to stimulate, record or modulate neural activity", in Neural Prostheses for Restoration of Sensory and Motor Function, Chapin JK et al (Eds.), CRC Press (1st edition, 2000).
Borovikova LV et al., "Vagus nerve stimulation attenuates the systemic inflammatory response to endotoxin," Nature 405(6785):458-62 (2000).
De Ferrari GM, "Vagal reflexes and survival during acute myocardial ischemia in conscious dogs with healed myocardial infarction," Am J Physiol 261(1 Pt 2):H63-9 (1991).
An Office Action dated Dec. 19, 2012, which issued during the prosecution of U.S. Appl. No. 12/228,630.
An Office Action dated Feb. 25, 2010, which issued during the prosecution of U.S. Appl. No. 11/975,646.
An Office Action dated Jul. 19, 2010, which issued during the prosecution of U.S. Appl. No. 11/975,646.
An Office Action dated Oct. 11, 2011, which issued during the prosecution of U.S. Appl. No. 11/978,776.
An Office Action dated Jul. 31, 2008, which issued during the prosecution of U.S. Appl. No. 11/347,120.
An Office Action dated Apr. 15, 2009, which issued during the prosecution of U.S. Appl. No. 11/347,120.
An Office Action dated Oct. 7, 2010, which issued during the prosecution of U.S. Appl. No. 11/347,120.
An Office Action dated Jan. 11, 2006, which issued during the prosecution of U.S. Appl. No. 10/205,475.
An Office Action dated Oct. 23, 2006, which issued during the prosecution of U.S. Appl. No. 10/205,475.
An Office Action dated Feb. 26, 2007, which issued during the prosecution of U.S. Appl. No. 10/205,475.
An Office Action dated Aug. 6, 2009, which issued during the prosecution of U.S. Appl. No. 10/205,475.
A Notice of Allowance dated May 14, 2010, which issued during the prosecution of U.S. Appl. No. 10/205,475.
U.S. Non-Final Office Action dated Feb. 21, 2014, issued in corresponding U.S. Appl. No. 13/661,512.

\* cited by examiner

ELECTRODE CUFFS

FIELD OF THE APPLICATION

The present invention relates generally to electrical stimulation of tissue, and specifically to methods and devices for regulating the stimulation of nerves or other tissue.

BACKGROUND

A number of patents and articles describe methods and devices for stimulating nerves to achieve a desired effect. Often these techniques include a design for an electrode or electrode cuff.

SUMMARY OF THE APPLICATION

In some applications of the present invention, an electrode assembly comprises a cuff and one or more electrodes. The cuff comprises an electrically-insulating material, and is shaped so as to define a tubular housing. The housing is shaped so as to define two edges and a longitudinal slit between the two edges. The slit and edges extend along an entire length of the cuff. The housing is configured to assume (a) an open position, in which the two edges do not touch each other, and (b) a closed position, in which (i) respective contact surfaces of the two edges touch each other, and (ii) the housing defines an inner surface that faces and surrounds a longitudinal axis of the housing. The electrodes are fixed to the inner surface.

For some applications, the cuff is shaped so as to define three or more annular insulating elements that extend toward the axis from the inner surface of the housing at respective longitudinal positions along housing. When the housing is in the closed position, the inner surface and pairs of the insulating elements are shaped so as to define, at respective longitudinal positions along the housing, respective chambers open toward the axis. For some applications, one or more of the electrodes are fixed within respective ones of chambers.

For some applications, the contact surfaces of the two edges extend toward the axis and protrude into the chambers. This configuration provides greater surface contact between the contact surfaces than if the contact surfaces did not extend into the chambers. This greater surface contact causes the contact surfaces to form a better electrical seal with each other, thereby reducing current leakage from the cuff.

For some applications, at least one of the electrodes comprises a strip of metal foil having two end portions and a central portion between the end portions. The central portion is disposed against the inner surface of the housing such that, when the housing is in the closed position, the central portion forms a partial ring around the axis that defines an exposed, electrically-conductive surface of the central portion, which exposed surface faces the axis. At least one of the end portions is shaped so as to define a curved portion that is embedded in and completely surrounded by the insulating material of the cuff, thereby fixing the end portion to the insulating material. This curved portion helps firmly secure the electrode to the insulating material of the cuff. Typically, the curved portion has an average radius of curvature that is less than 10% of a length of the central portion measured around axis, such as less than 5%, e.g., less than 3%.

There is therefore provided, in accordance with an application of the present invention, apparatus including an electrode assembly, which includes:
one or more electrodes; and
a cuff, which includes an electrically insulating material, and which is shaped so as to define:
a tubular housing that defines a longitudinal axis thereal ong, the housing shaped so as to define two edges and a slit between the two edges, which slit and edges extend along an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis, to which inner surface the electrodes are fixed, and
three or more annular insulating elements that extend toward the axis from the inner surface of the housing at respective longitudinal positions along the housing, such that, when the housing is in the closed position, the inner surface of the housing and pairs of the insulating elements are shaped so as to define, at respective longitudinal positions along the housing, respective chambers open toward the axis,
wherein the housing is shaped such that the contact surfaces of the two edges extend toward the axis and protrude into the chambers.

For some applications, the housing is shaped such that the slit and the edges extend parallel to the axis along the entire length of the cuff.

For some applications, the cuff is shaped such that the insulating elements and the contact surfaces extend to a same average distance from the axis.

For some applications, the cuff is shaped such that a first average distance that the contact surfaces extend from the inner surface toward the axis is less than a second average distance that the insulating elements extend from the inner surface toward the axis.

For some applications, the housing is shaped such that an average distance that the first contact surfaces extend from the inner surface toward the axis is at least 0.6 mm.

For any of the applications described above, the electrodes may be shaped as partial rings, both when the housing is in the open position and when the housing is in the closed position.

For any of the applications described above, two of the insulating elements may be disposed at respective longitudinal ends of the tubular housing.

For any of the applications described above, the entire length of the cuff may be between 1 and 40 mm, such as between 5 and 20 mm For any of the applications described above, at least one of the electrodes may be fixed to the inner surface within one of the chambers.

For any of the applications described above, the cuff may be shaped so as to be placeable around an elliptical cylinder having a major axis that is between 1 and 8 mm and a minor axis that is between 0.5 and 6 mm, and to assume the closed position when thus placed.

There is further provided, in accordance with an application of the present invention, apparatus including an electrode assembly, which includes:
a cuff, which includes an electrically insulating material, and which is shaped so as to define a tubular housing that defines a longitudinal axis therealong, the housing shaped so as to define two edges and a slit between the two edges, which slit and edges extend along an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis; and
one or more electrodes, at least one of which includes a strip of metal foil having two end portions and a central portion between the end portions, wherein the central portion is disposed against the inner surface of the housing such that, when the housing is in the closed position, the central portion forms a partial ring around the axis that defines an exposed surface of the central portion, which exposed surface faces the axis, and wherein at least one of the end portions is shaped so as to define a curved portion that is embedded in and completely surrounded by the insulating material, thereby fixing the end portion to the insulating material, the curved portion having an average radius of curvature that is less than 10% of a length of the central portion measured around the axis.

For some applications, the average radius of curvature of the curved portion is less than 5% of the length of the central portion measured around the axis.

For some applications, the housing is shaped such that the slit and the edges extend parallel to the axis along the entire length of the cuff.

For any of the applications described above, the average radius of curvature of the curved portion may be less than 1.5 mm, such as less than 0.5 mm For any of the applications described above, the strip of metal foil may be shaped such that a direction of curvature of the curved portion is opposite a general direction of curvature of the central portion.

For any of the applications described above, the curved portion may be shaped so as to define an arc that subtends an angle of at least 90 degrees, such as at least 180 degrees, e.g., at least 270 degrees, such as at least 360 degrees.

For any of the applications described above, the curved portion, if straightened, may have a length of at least 1.5 mm, measured in a direction perpendicular to the axis. Alternatively or additionally, for any of the applications described above, the curved portion, if straightened, may have a length equal to at least 5% of an entire length of the strip of metal, if straightened, which lengths are measured in a direction perpendicular to the axis.

For any of the applications described above, the at least one of the two end portions may be a first one of the two end portions, the curved portion may be a first curved portion, and a second one of the two end portions may be shaped so as to define a second curved portion that is embedded in and completely surrounded by the insulating material, thereby fixing the second end portion to the insulating material, the second curved portion having an average radius of curvature that is less than 10% of the length of the central portion measured around the axis.

There is still further provided, in accordance with an application of the present invention, a method including:

providing an electrode assembly that includes (1) one or more electrodes, and (2) a cuff, which includes an electrically insulating material, and which is shaped so as to define (A) a tubular housing that defines a longitudinal axis therealong, the housing shaped so as to define two edges and a slit between the two edges, which slit and edges extend an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis, to which inner surface the electrodes are fixed, and (B) three or more annular insulating elements that extend toward the axis from the inner surface of the housing at respective longitudinal positions along the housing, such that, when the housing is in the closed position, the inner surface of the housing and pairs of the insulating elements are shaped so as to define, at respective longitudinal positions along the housing, respective chambers open toward the axis, wherein the housing is shaped such that the contact surfaces of the two edges extend toward the axis and protrude into the chambers;

while the housing is in the open position, placing the cuff around tubular body tissue of a subject; and coupling the cuff to the tubular body tissue by causing the housing to assume the closed position.

There is additionally provided, in accordance with an application of the present invention, a method including:

providing an electrode assembly that includes (1) a cuff, which includes an electrically insulating material, and which is shaped so as to define a tubular housing that defines a longitudinal axis therealong, the housing shaped so as to define two edges and a slit between the two edges, which slit and edges extend an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis, and (2) one or more electrodes, at least one of which includes a strip of metal foil having two end portions and a central portion between the end portions, wherein the central portion is disposed against the inner surface of the housing such that, when the housing is in the closed position, the central portion forms a partial ring around the axis that defines an exposed surface of the central portion, which exposed surface faces the axis, and wherein at least one of the end portions is shaped so as to define a curved portion that is embedded in and completely surrounded by the insulating material, thereby fixing the end portion to the insulating material, the curved portion having an average radius of curvature that is less than 10% of the length of the central portion measured around the axis;

while the housing is in the open position, placing the cuff around tubular body tissue of a subject; and coupling the cuff to the tubular body tissue by causing the housing to assume the closed position.

The present invention will be more fully understood from the following detailed description of embodiments thereof, taken together with the drawings, in which:

DETAILED DESCRIPTION OF APPLICATIONS

Figure 1A:
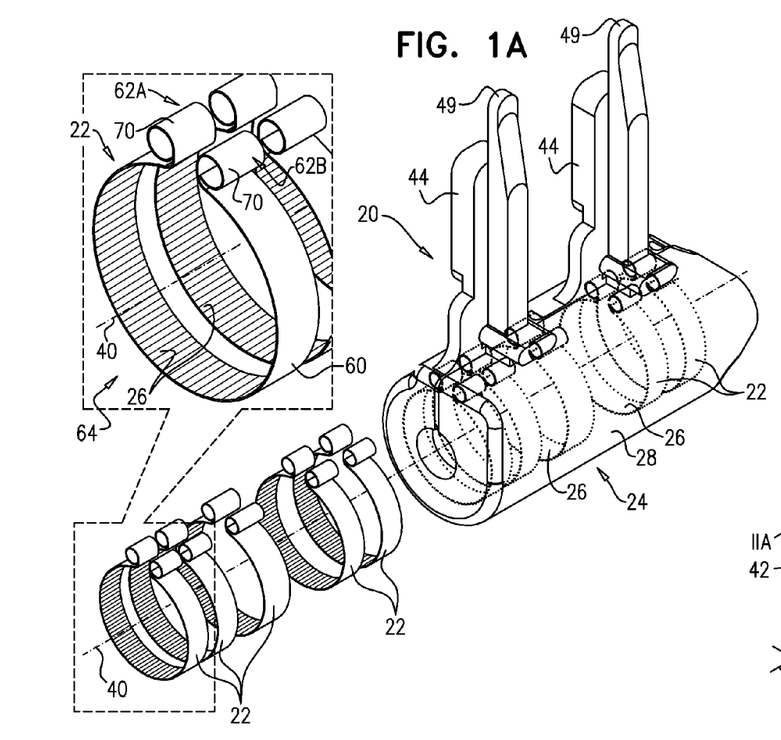
FIGS. 1A-C are schematic illustrations of an electrode assembly, in accordance with an application of the present invention.
Figure 1B:
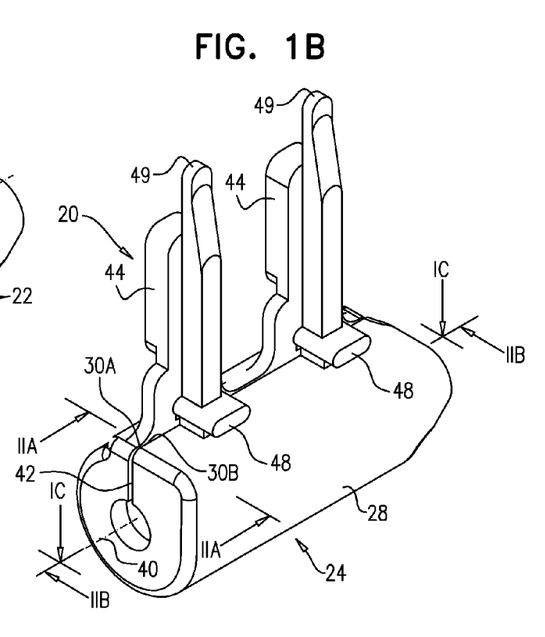
Figure 1C:
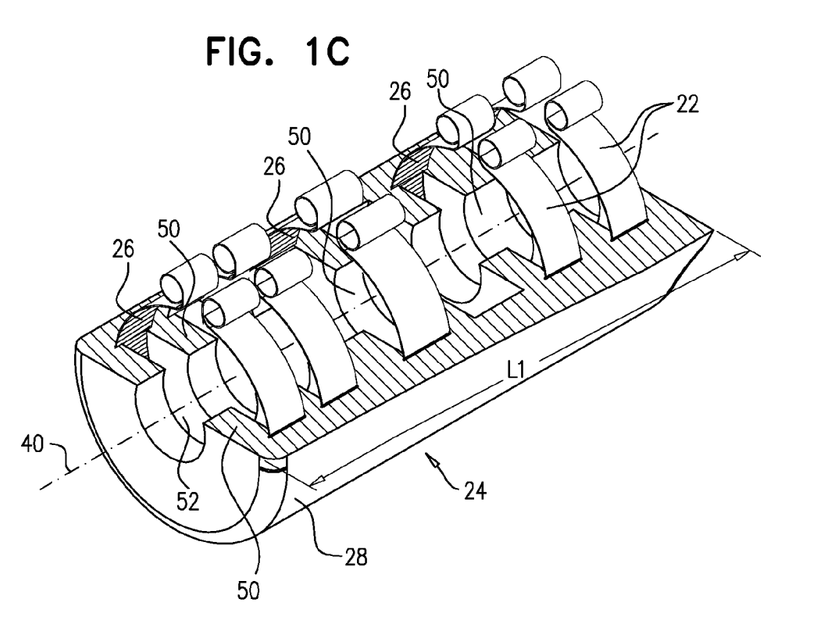

FIGS. 1A-C are schematic illustrations of an electrode assembly 20, in accordance with an application of the present invention. Electrode assembly 20 comprises a cuff 24 and one or more electrodes 22. For clarity of illustration, electrodes 22 are shown twice in FIG. 1A, both removed from cuff 24 (at the left side of the figure) and disposed within the cuff; in actual practice, the electrodes are disposed within the cuff, as shown at the right side of the figure and in the other figures. FIG. 1C is a cut-away illustration of electrode assembly 20, in which a portion of cuff 24 is not shown in order to better illustrate electrodes 22. Electrodes 22 are fixed to cuff 24 such that the electrodes define respective exposed surfaces 26 facing axis 40.

Cuff 24 is shaped so as to define a tubular housing 28 that defines and at least partially surrounds (typically entirely surrounds) a longitudinal axis 40 therealong. Cuff 24 is configured to be placed at least partially around (typically entirely around) a nerve or other tubular body tissue, such as a blood vessel, a muscle, a tendon, a ligament, an esophagus, intestine, a fallopian tube, a neck of a gall bladder, a cystic duct, a hepatic duct, a common hepatic duct, a bile duct, and/or a common bile duct. Alternatively or additionally, cuff 24 is configured to be placed at least partially around (typically entirely around) an elliptical (e.g., circular) cylinder, which, for example, may have a major axis that is between 1 and 8 mm and a minor axis that is between 0.5 and 6 mm. As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular, circular, or irregularly shaped.

Cuff 24 comprises an elastic, electrically-insulating material such as silicone or a silicone copolymer, which may have, for example, a hardness of between about 10 Shore A and about 90 Shore A, such as about 40 Shore A. Optionally, cuff 24 comprises more than one material; for example, housing 28 and insulating elements 50, described hereinbelow, may comprise different materials, e.g., may comprise silicone having different hardnesses.

Electrode assembly 20 optionally further comprises a lead assembly, which comprises one or more electrical leads, as is known in the art. For example, the lead assembly may be implemented as described in U.S. application Ser. No. 12/952,058, filed Nov. 22, 2010, which is assigned to the assignee of the present application and is incorporated herein by reference. The leads are coupled to all or a portion of electrodes 22. The lead assembly couples electrode assembly 20 to an implanted or external control unit, which comprises appropriate circuitry for driving current between two or more of electrodes 22, as is known in the art. Typically, the control unit configures the current such that one or more of the contact surfaces function as cathodes, and one or more function as anodes, such as described hereinbelow with reference to Tables 1 and 2.

Figure 2A:
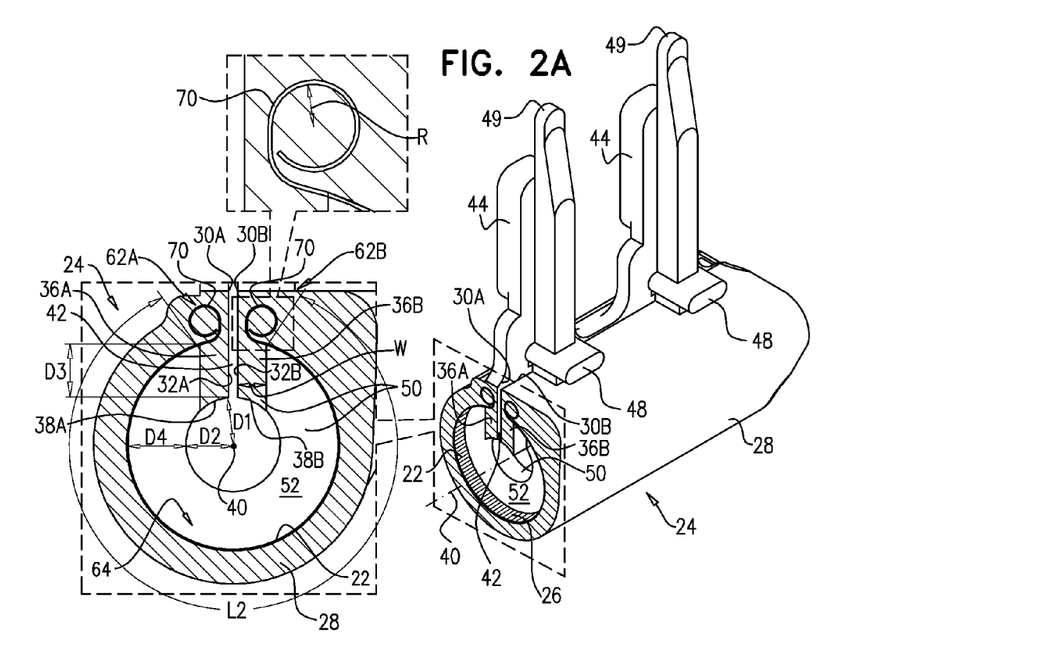
FIGS. 2A and 2B are schematic illustrations of a cuff of the electrode assembly of FIGS. 1A-C in slightly open and closed positions, respectively, in accordance with an application of the present invention.
Figure 2B:
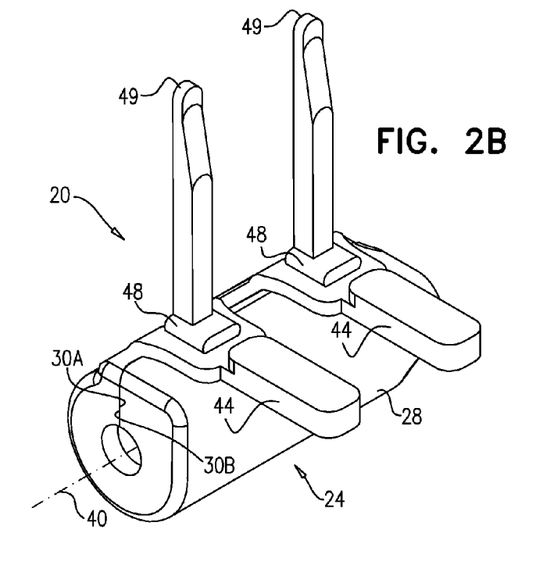

Reference is now made to FIGS. 2A and 2B, which are schematic illustrations of cuff 24 in slightly open and closed positions, respectively, in accordance with an application of the present invention. Housing 28 is shaped so as to define two edges 30A and 30B and a longitudinal slit 42 between the two edges. The slit and edges extend along an entire length of the cuff 24, typically parallel to axis 40. The housing is configured to assume:
 an open position, as shown in FIG. 2A, in which two edges 30A and 30B do not touch each other; and
 a closed position, as shown in FIG. 2B, in which (i) respective contact surfaces 32A and 32B of edges 30A and 30B touch each other, and (ii) the housing defines an inner surface 34 that faces and surrounds axis 40.

The cuff is placed around the tubular body tissue (such as a nerve) or elliptical cylinder (such as described above) by passing the tubular body tissue or cylinder through the slit when the housing is in the open position. The edges of the slit are brought together to bring the housing into the closed position.

Electrodes 22 are fixed to inner surface 34. Typically, electrodes 22 are shaped as partial rings, both when the housing is in the open position and when the housing is in the closed position. For some applications, electrodes 22 comprise respective strips of metal foil 60, such as described hereinbelow with reference to FIGS. 1A-C and 2A-B.

For some applications, electrode assembly 20 further comprises one or more closing elements 44, which are configured to hold edges 30A and 30B together. For some applications, each of the closing elements comprises an opening 46 near one edge 30A (labeled in FIG. 3) and a corresponding protrusion 48 on other edge 30B. To close the cuff, each of the protrusions is inserted into the corresponding slit. Optionally, each of the closing elements further comprises a tab 49, which the surgeon implanting the cuff may grasp to help pull protrusion 48 through opening 46.

Figure 3:
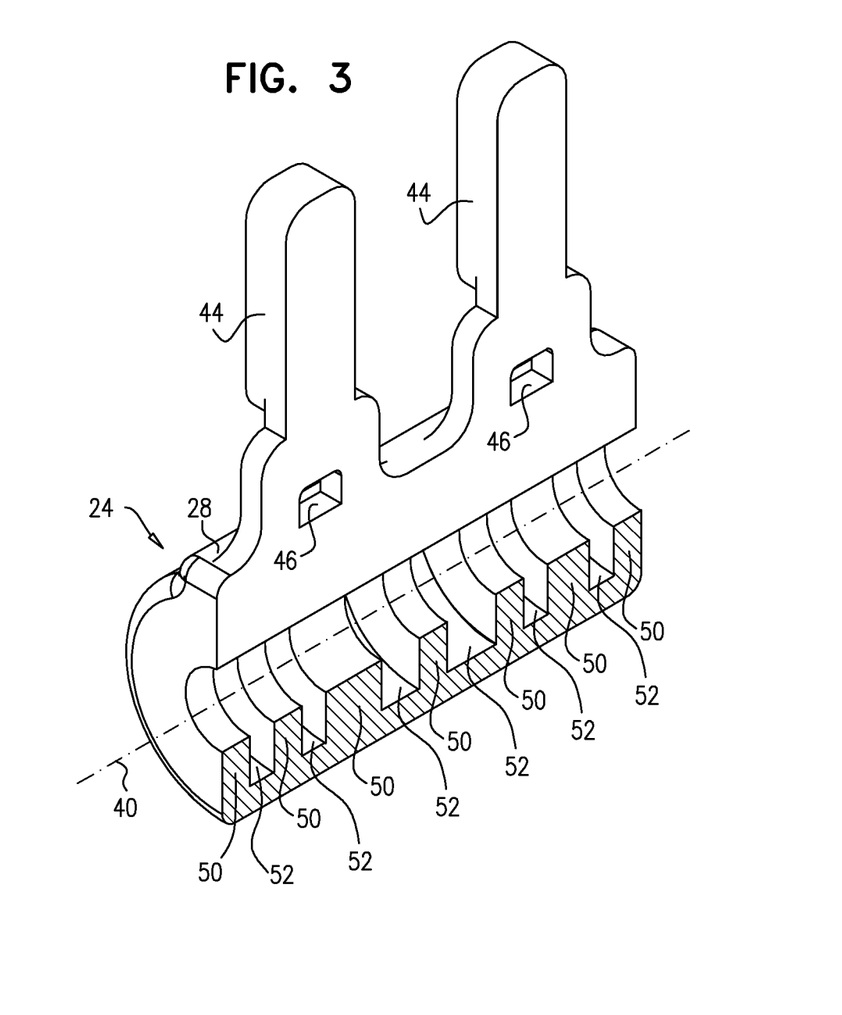
FIG. 3 is a schematic cut-away illustration of the cuff of FIGS. 2A and 2B, in accordance with an application of the present invention.

Reference is again made to FIGS. 1C and 2A-B, as well as to FIG. 3, which is a schematic cut-away illustration of cuff 24, in accordance with an application of the present invention. For clarity of illustration, electrodes 22 are not shown in FIG. 3. Cuff 24 is shaped so as to define three or more annular insulating elements 50, which extend toward axis 40 from inner surface 34 of housing 28 at respective longitudinal positions along housing 28. In the exemplary configuration shown in the figures, cuff 24 is shaped so as to define seven annular insulating elements 50, two of which are disposed at respective longitudinal ends of the cuff, and five of which are disposed longitudinally within the cuff. When housing 28 is in the closed position, inner surface 34 and pairs of insulating elements 50 are shaped so as to define, at respective longitudinal positions along housing 28, respective chambers 52 open toward axis 40. (In FIGS. 2A and 2B, a longitudinal portion of cuff 24 has been cut away in order to show the inside of a longitudinal portion of one of chambers 52.) In the exemplary configuration shown in the figures, cuff 24 is shaped so as to define six annular chambers 52. For some applications, one or more of electrodes 22 are fixed within respective ones of chambers 52, typically to inner surface 34. For some applications, each of chambers 52 has a longitudinal length along the cuff of at least 0.3 mm, no more than 5 mm, and/or between 0.3 and 5 mm. For some applications, during manufacture, housing 28 and insulating elements 50 are molded as a single piece that is shaped so as to define the housing and the insulating elements. Alternatively, the insulating elements are fabricated as separate pieces and subsequently affixed to the housing.

For some applications, as best seen in FIGS. 2A and 2B, housing 28 is shaped such that contact surfaces 32A and 32B of two edges 30A and 30B extend toward axis 40 and protrude into chambers 52. Respective portions of the material of the housing define two protrusions 36A and 36B, which extend toward the axis and protrude into the chambers, and which define the portions of contact surfaces 32A and 32B, respectively, that extend toward the axis and protrude into the chambers. This configuration provides greater surface contact between contact surfaces 32A and 32B than if the contact surfaces did not extend into the chambers. This greater surface contact causes the contact surfaces to form a better electrical seal with each other, thereby reducing current leakage from the cuff.

Contact surfaces 32A and 32B extend radially inward to an average distance D1 from axis 40. For some applications, average distance D1 is at least 0.5 mm, no more than 3 mm, and/or between 0.5 and 3 mm, such as at least 1.1 mm, no more than 1.8 mm, and/or between 1.1 and 1.8 mm Insulating elements 50 extend radially inward to an average distance D2 from axis 40. For some applications, average distance D2 is at least 0.5 mm, no more than 3 mm, and/or between 0.5 and 3 mm, such as at least 1.1 mm, no more than 1.8 mm, and/or between 1.1 and 1.8 mm. For some applications, average distance D2 is less for the insulating elements at the longitudinal ends of the cuff than for the insulating elements disposed longitudinally within the cuff. For some applications, average distance D1 equals average distance D2; in other words, insulating elements 50 and contact surfaces 32A and 32B extend to a same average distance from axis 40. For these applications, protrusions 36A and 36B define surfaces 38A and 38B, respectively, which face axis 40; surfaces 38A and 38B may have the same curvature as the surfaces of insulating elements 50 that face the axis, such as shown in FIG. 2A.

Contact surfaces 32A and 32B extend radially inward a first average distance D3 from inner surface 34 toward axis 40. For some applications, average distance D3 is at least 0.1 mm, no more than 3 mm, and/or between 0.1 and 3 mm, such as at least 0.3 mm, no more than 1.5 mm, and/or between 0.3 and 1.5 mm Insulating elements 50 extend radially inward a second average distance D4 from inner surface 34 toward axis 40. For some applications, average distance D4 is at least 0.1 mm, no more than 3 mm, and/or between 0.1 and 3 mm, such as at least 0.3 mm, no more than 1.5 mm, and/or between 0.3 and 1.5 mm. For some applications, first average distance D3 is less than second average distance D4. Each of protrusions 36A and 36B has a width W, measured in a direction perpendicular to both (a) axis 40 and (b) contact surfaces 32A and 32B, respectively, when cuff 24 is in the closed position. For some applications, width W is at least 0.3 mm, no more than 2 mm, and/or between 0.3 and 2 mm Reference is again made to FIG. 1C. For some applications, an entire length L1 of cuff 24, measured along longitudinal axis 40, is at least 1 mm, no more than 40 mm, and/or between 1 and 40 mm, e.g., at least 5 mm, no more than 20 mm, and/or between 5 and 20 mm, such as 12 mm Reference is again made to FIGS. 1A-C and 2A-B. For some applications, at least one of electrodes 22 comprises strip of metal foil 60, which has two end portions 62A and 62B and a central portion 64 between the end portions. Central portion 64 is disposed against inner surface 34 of housing 28 such that, when the housing is in the closed position, the central portion forms a partial ring around axis 40 that defines exposed, electrically-conductive surface 26 of the central portion, which exposed surface 26 faces the axis (exposed surfaces 26 of the electrodes are shaded in the figures). (It is noted that the ring is not necessarily partially or entirely curved (as shown in the figures), and may optionally include one or more straight portions.) Typically, all of the electrodes comprise respective strips of metal foil 60.

In this configuration, at least one of end portions 62A and 62B is shaped so as to define a curved portion 70 that is embedded in and completely surrounded by the insulating material of cuff 24, thereby fixing the end portion to the insulating material. This curved portion helps firmly secure the electrode to the insulating material of the cuff by enforcing the mechanical connection between the electrode and the insulating material. Typically, curved portion 70 has an average radius of curvature R that is less than 10% of a length L2 of central portion 64 measured around axis 40, such as less than 5%, e.g., less than 3%. This degree of curvature helps firmly secure the electrode to the insulating material; if the curved portion were less curved, the electrode would not be as firmly secured to the insulating material. Typically, both of end portions 62A and 62B comprise respective curved portions 70 having the characteristics described herein. (As used in the present application, including in the claims, length L2 "measured around the axis" is to be understood as the length of central portion 64 measured in a direction perpendicular to axis 40, if the central portion were to be flattened, i.e., unrolled. This length may also be considered the "circumferential" length of central portion 64, even though central portion 64 typically does not form a complete loop, such as a complete ellipse or circle.)

For some applications, average radius of curvature R is less than 1.5 mm, e.g., less than 1 mm, such as less than 0.5 mm, and/or at least 0.2 mm, e.g., between 0.25 mm and 0.5 mm, such as 0.25 mm or 0.35 mm. Alternatively or additionally, for some applications, length L2 is at least 10 mm, no more than 20 mm, and/or between 10 mm and 20 mm, such as about 14 mm.

For some applications, as shown in the figures, strip of metal foil 60 is shaped such that a direction of curvature of curved portion 70 is opposite a general direction of curvature of central portion 64. For example, a general direction of curvature of central portion 64 as approaching end portion 62B is counterclockwise, which transitions to clockwise along curved portion 70 of end portion 62B.

Typically, curved portion 70 is shaped so as to define an arc that subtends an angle of at least 90 degrees, such as at least 180 degrees, at least 270 degrees, or at least 360 degrees. (In the figures, curved portion 70 is shows subtending an angle of slightly greater than 360 degrees, i.e., a full circle with slightly overlapping end portions.) For some applications, curved portion 70, if straightened, would have a length of at least 1.5 mm, measured in a direction perpendicular to axis 40. Alternatively or additionally, for some applications, curved portion 70, if straightened, would have a length equal to at least 5% of an entire length of the strip of metal foil 60, if straightened, which lengths are measured in a direction perpendicular to axis 40.

As mentioned above, for some applications, one or more of electrodes 22 are fixed within respective ones of chambers 52. The following tables set forth two exemplary distributions of the electrodes in the chambers. The tables also indicate, by way of example, which of the electrodes are configured by a control unit to function as cathode(s), which as anode(s), and which as passive electrode(s). Each of the passive electrodes is coupled to at least one other passive electrode, and is electrically device-coupled to neither (a) any circuitry that is electrically device-coupled to at least one cathode or at least one anode, nor (b) an energy source. The passive electrodes may be implemented using techniques described in U.S. Pat. No. 7,627,384 to Ayal et al., which is incorporated herein by reference. The chambers are numbered from left to right in FIGS. 1A and 1C.

TABLE 1

| Chamber | Electrode type |
|---|---|
| 1 | Passive electrode |
| 2 | Anode |
| 3 | Cathode |
| 4 | Empty chamber (no electrode) |
| 5 | Cathode |
| 6 | Passive electrode |

TABLE 2

| Segment | Electrode type |
|---|---|
| 1 | Passive electrode |
| 2 | Cathode |
| 3 | Anode |

TABLE 2-continued

| Segment | Electrode type |
|---|---|
| 4 | Empty chamber (no electrode) |
| 5 | Anode |
| 6 | Passive electrode |

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 10/205,475, filed Jul. 24, 2002, which issued as U.S. Pat. No. 7,778,703, U.S. patent application Ser. No. 10/205,474, filed Jul. 24, 2002, which issued as U.S. Pat. No. 6,907,295, International Patent Application PCT/IL03/00431, filed May 23, 2003, which published as PCT Publication WO 03/099377, U.S. patent application Ser. No. 10/529,149, which published as US Patent Application Publication 2006/0116739, U.S. patent application Ser. No. 10/719,659, filed Nov. 20, 2003, which issued as U.S. Pat. No. 7,778,711, U.S. patent application Ser. No. 11/022,011, filed Dec. 22, 2004, which issued as U.S. Pat. No. 7,561,922, U.S. patent application Ser. No. 11/234,877, filed Sep. 22, 2005, which issued as U.S. Pat. No. 7,885,709, U.S. patent application Ser. No. 11/280,884, filed Nov. 15, 2005, which issued as U.S. Pat. No. 7,627,384, U.S. patent application Ser. No. 12/217,930, filed Jul. 9, 2008, which published as US Patent Application Publication 2010/0010603, U.S. patent application Ser. No. 11/347,120, filed Feb. 2, 2006, which issued as U.S. Pat. No. 7,844,346, U.S. patent application Ser. No. 12/228,630, filed Aug. 13, 2008, which published as US Patent Application Publication 2010/0042186, U.S. patent application Ser. No. 12/947,608, filed Nov. 16, 2010, which published as US Patent Application Publication 2011/0098796, and/or U.S. patent application Ser. No. 12/952,058, filed Nov. 22, 2010.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an electrode assembly, which comprises:
    one or more electrodes; and
    a cuff, which comprises an electrically insulating material, and which is shaped so as to define:
        a tubular housing that defines a longitudinal axis therealong, the housing shaped so as to define two edges and a slit between the two edges, which slit and edges extend along an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis, to which inner surface the electrodes are fixed, and
    three or more annular insulating elements that extend toward the axis from the inner surface of the housing at respective longitudinal positions along the housing, such that, when the housing is in the closed position, the inner surface of the housing and pairs of the insulating elements are shaped so as to define, at respective longitudinal positions along the housing, respective chambers open toward the axis,
    wherein the housing is shaped such that the contact surfaces of the two edges extend toward the axis and protrude into the chambers.

2. The apparatus according to claim 1, wherein the housing is shaped such that the slit and the edges extend parallel to the axis along the entire length of the cuff.

3. The apparatus according to claim 1, wherein the cuff is shaped such that the insulating elements and the contact surfaces extend to a same average distance from the axis.

4. The apparatus according to claim 1, wherein the cuff is shaped such that a first average distance that the contact surfaces extend from the inner surface toward the axis is less than a second average distance that the insulating elements extend from the inner surface toward the axis.

5. The apparatus according to claim 1, wherein the housing is shaped such that an average distance that the first contact surfaces extend from the inner surface toward the axis is at least 0.6 mm.

6. The apparatus according to claim 1, wherein the electrodes are shaped as partial rings, both when the housing is in the open position and when the housing is in the closed position.

7. The apparatus according to claim 1, wherein two of the insulating elements are disposed at respective longitudinal ends of the tubular housing.

8. The apparatus according to claim 1, wherein the entire length of the cuff is between 1 and 40 mm.

9. The apparatus according to claim 8, wherein the entire length of the cuff is between 5 and 20 mm.

10. The apparatus according to claim 1, wherein at least one of the electrodes is fixed to the inner surface within one of the chambers.

11. The apparatus according to claim 1, wherein the cuff is shaped so as to be placeable around an elliptical cylinder having a major axis that is between 1 and 8 mm and a minor axis that is between 0.5 and 6 mm, and to assume the closed position when thus placed.

12. Apparatus comprising an electrode assembly, which comprises:
    a cuff, which comprises an electrically insulating material, and which is shaped so as to define a tubular housing that defines a longitudinal axis therealong, the housing shaped so as to define two edges and a slit between the two edges, which slit and edges extend along an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis; and
    one or more electrodes, at least one of which comprises a strip of metal foil having two end portions and a central portion between the end portions,
    wherein the central portion is disposed against the inner surface of the housing such that, when the housing is in the closed position, the central portion forms a partial ring around the axis that defines an exposed surface of the central portion, which exposed surface faces the axis, and wherein at least one of the end portions is shaped so as to define a curved portion that is embedded in and completely surrounded by the insulating material, thereby fixing the end portion to the insulating material, the curved portion having an average radius of curvature that is less than 10% of a length of the central portion measured around the axis.

13. The apparatus according to claim 12, wherein the average radius of curvature of the curved portion is less than 5% of the length of the central portion measured around the axis.

14. The apparatus according to claim 12, wherein the housing is shaped such that the slit and the edges extend parallel to the axis along the entire length of the cuff.

15. The apparatus according to claim 12, wherein the average radius of curvature of the curved portion is less than 1.5 mm.

16. The apparatus according to claim 15, wherein the average radius of curvature of the curved portion is less than 0.5 mm.

17. The apparatus according to claim 12, wherein the strip of metal foil is shaped such that a direction of curvature of the curved portion is opposite a general direction of curvature of the central portion.

18. The apparatus according to claim 12, wherein the curved portion is shaped so as to define an arc that subtends an angle of at least 90 degrees.

19. The apparatus according to claim 18, wherein the angle is at least 180 degrees.

20. The apparatus according to claim 19, wherein the angle is at least 270 degrees.

21. The apparatus according to claim 20, wherein the angle is at least 360 degrees.

22. The apparatus according to claim 12, wherein the curved portion, if straightened, would have a length of at least 1.5 mm, measured in a direction perpendicular to the axis.

23. The apparatus according to claim 12, wherein the curved portion, if straightened, would have a length equal to at least 5% of an entire length of the strip of metal, if straightened, which lengths are measured in a direction perpendicular to the axis.

24. The apparatus according to claim 12, wherein the at least one of the two end portions is a first one of the two end portions, and wherein the curved portion is a first curved portion, and wherein a second one of the two end portions is shaped so as to define a second curved portion that is embedded in and completely surrounded by the insulating material, thereby fixing the second end portion to the insulating material, the second curved portion having an average radius of curvature that is less than 10% of the length of the central portion measured around the axis.

25. A method comprising:

providing an electrode assembly that includes (1) one or more electrodes, and (2) a cuff, which comprises an electrically insulating material, and which is shaped so as to define (A) a tubular housing that defines a longitudinal axis therealong, the housing shaped so as to define two edges and a slit between the two edges, which slit and edges extend an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis, to which inner surface the electrodes are fixed, and (B) three or more annular insulating elements that extend toward the axis from the inner surface of the housing at respective longitudinal positions along the housing, such that, when the housing is in the closed position, the inner surface of the housing and pairs of the insulating elements are shaped so as to define, at respective longitudinal positions along the housing, respective chambers open toward the axis, wherein the housing is shaped such that the contact surfaces of the two edges extend toward the axis and protrude into the chambers;

while the housing is in the open position, placing the cuff around tubular body tissue of a subject; and coupling the cuff to the tubular body tissue by causing the housing to assume the closed position.

26. A method comprising:

providing an electrode assembly that includes (1) a cuff, which comprises an electrically insulating material, and which is shaped so as to define a tubular housing that defines a longitudinal axis therealong, the housing shaped so as to define two edges and a slit between the two edges, which slit and edges extend an entire length of the cuff, wherein the housing is configured to assume (a) an open position, in which the two edges do not touch each other, and (b) a closed position, in which (i) respective contact surfaces of the two edges touch each other, and (ii) the housing defines an inner surface that faces and surrounds the axis, and (2) one or more electrodes, at least one of which comprises a strip of metal foil having two end portions and a central portion between the end portions, wherein the central portion is disposed against the inner surface of the housing such that, when the housing is in the closed position, the central portion forms a partial ring around the axis that defines an exposed surface of the central portion, which exposed surface faces the axis, and wherein at least one of the end portions is shaped so as to define a curved portion that is embedded in and completely surrounded by the insulating material, thereby fixing the end portion to the insulating material, the curved portion having an average radius of curvature that is less than 10% of the length of the central portion measured around the axis;

while the housing is in the open position, placing the cuff around tubular body tissue of a subject; and coupling the cuff to the tubular body tissue by causing the housing to assume the closed position.

\* \* \* \* \*